(12) United States Patent
Kim

(10) Patent No.: US 11,827,939 B2
(45) Date of Patent: Nov. 28, 2023

(54) METHOD FOR DIAGNOSING CHOLANGIOCARCINOMA VIA BACTERIAL METAGENOMIC ANALYSIS

(71) Applicant: MD HEALTHCARE INC., Seoul (KR)

(72) Inventor: Yoon-Keun Kim, Gyeonggi-do (KR)

(73) Assignee: MD HEALTHCARE INC., Seoul (KR)

( * ) Notice: Subject to any disclaimer, the term of this patent is extended or adjusted under 35 U.S.C. 154(b) by 0 days.

(21) Appl. No.: 16/957,536

(22) PCT Filed: Jan. 18, 2019

(86) PCT No.: PCT/KR2019/000784
§ 371 (c)(1),
(2) Date: Jun. 24, 2020

(87) PCT Pub. No.: WO2019/146966
PCT Pub. Date: Aug. 1, 2019

(65) Prior Publication Data
US 2021/0102259 A1 Apr. 8, 2021

(30) Foreign Application Priority Data

Jan. 23, 2018 (KR) .......................... 10-2018-0008259

(51) Int. Cl.
*C12Q 1/6886* (2018.01)
*C12Q 1/689* (2018.01)
*C12Q 1/6895* (2018.01)

(52) U.S. Cl.
CPC .......... *C12Q 1/6886* (2013.01); *C12Q 1/689* (2013.01); *C12Q 1/6895* (2013.01); *C12Q 2531/113* (2013.01)

(58) Field of Classification Search
None
See application file for complete search history.

(56) References Cited

U.S. PATENT DOCUMENTS

2017/0260580 A1* 9/2017 Nouri Zad .......... C12Q 1/6846

FOREIGN PATENT DOCUMENTS

| AU | 2015203111 A1 | 7/2015 | |
|----|---------------|--------|--|
| AU | 2015268602 A1 | 1/2016 | |
| CN | 102549143 A | 7/2012 | |
| CN | 106916889 A | 7/2017 | |
| CN | 106999523 A | 8/2017 | |
| CN | 107429290 A | 12/2017 | |
| EP | 2484752 A2 * | 8/2012 | ............. A61P 31/04 |
| KR | 20110025068 A | 3/2011 | |
| KR | 20110025603 A | 3/2011 | |
| KR | 20160073157 A | 6/2016 | |
| WO | 2017009693 A1 | 1/2017 | |
| WO | 2017061878 A1 | 4/2017 | |

OTHER PUBLICATIONS

Chng, K.R. et al., "Tissue Microbiome Profiling Identifies an Enrichment of Specific Enteric Bacteria in Opisthorchis viverrini Associated Cholangiocarcinoma", EBioMedicine, 2016, vol. 8, pp. 195-202.
Chinese Office Action for App. No. CN201980009542.6, dated Dec. 2, 2021, 9 pages.
English translation of Chinese Office Action for App. No. CN201980009542.6, dated Dec. 2, 2021, 9 pages.
Jiong-huang Chen et al., Journal of Zhejiang University-Science B (Biomedicine & Biotechnology), 07, Jul. 3, 2016, 537-544.
Jordan Pleskatt et al., "Infection with the carcinogenic liver fluke Opisthorchis viverrini modifies intestinal and biliary microbiome" FASEB, 27, Aug. 7, 2013, 4572-458.

* cited by examiner

*Primary Examiner* — Katherine D Salmon
(74) *Attorney, Agent, or Firm* — Riverside Law LLP

(57) ABSTRACT

The present invention relates to a method of diagnosing cholangiocarcinoma through bacterial metagenomic analysis, and more particularly to a method of diagnosing cholangiocarcinoma by analyzing an increase or decrease in content of specific bacteria-derived extracellular vesicles through bacterial metagenomic analysis using subject-derived samples. Extracellular vesicles secreted from bacteria present in the environment are absorbed into the body, and can directly affect the occurrence of cancer, and cholangiocarcinoma is difficult to diagnose early before symptoms appear so that effective treatment is difficult. Therefore, by previous diagnosis of the risk for the onset of cholangiocarcinoma through metagenomic analysis of bacterial extracellular vesicles using human-derived samples according to the present invention, the risk group of cholangiocarcinoma can be diagnosed and predicted early to delay or prevent the onset of cholangiocarcinoma through proper management, and early diagnosis can be performed even after the onset, thereby reducing the incidence of cholangiocarcinoma and increasing the therapeutic effect. In addition, the progression of cancer can be improved or the recurrence of cancer may be prevented by avoiding the exposure of causative factors through metagenomic analysis for patients diagnosed with cholangiocarcinoma.

3 Claims, 7 Drawing Sheets
Specification includes a Sequence Listing.

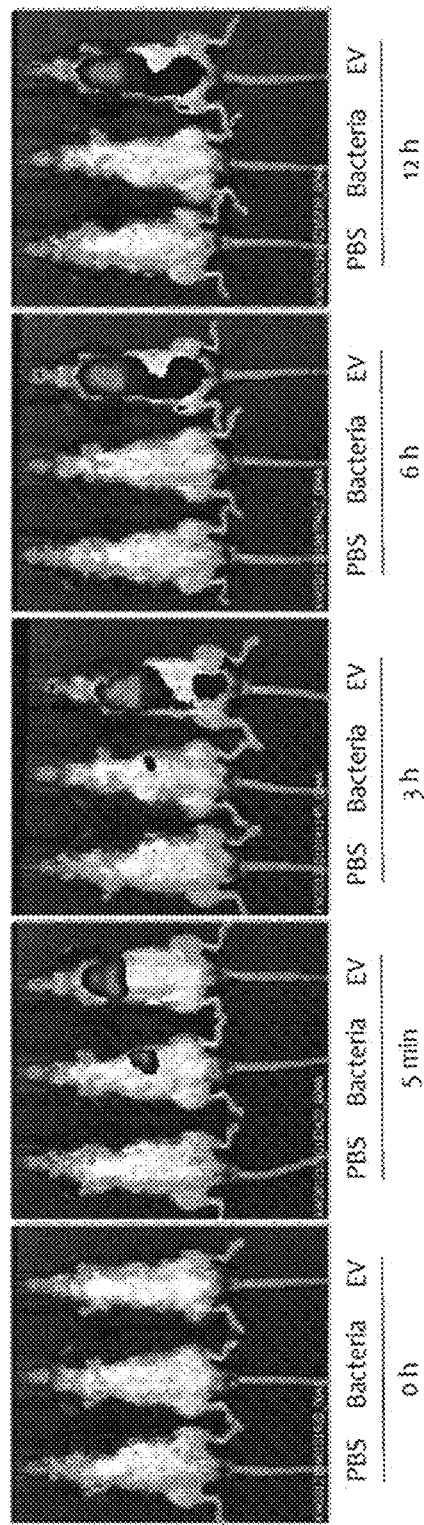

```
                         SEQUENCE LISTING

<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: 16S_V3_F
<220> FEATURE:
<221> NAME/KEY: misc_feature
<222> LOCATION: (42)..(42)
<223> OTHER INFORMATION: n is a, c, g, or t

<400> SEQUENCE: 1
tcgtcggcag cgtcagatgt gtataagaga cagcctacgg gnggcwgcag                 50

<210> SEQ ID NO 2
<211> LENGTH: 55
<212> TYPE: DNA
<213> ORGANISM: Artificial Sequence
<220> FEATURE:
<223> OTHER INFORMATION: 16S_V4_R

<400> SEQUENCE: 2
gtctcgtggg ctcggagatg tgtataagag acaggactac hvgggtatct aatcc           55
```

METHOD FOR DIAGNOSING CHOLANGIOCARCINOMA VIA BACTERIAL METAGENOMIC ANALYSIS

CROSS-REFERENCE TO RELATED APPLICATIONS

This application is the U.S. national phase application filed under 35 U.S.C. § 371 claiming benefit to International Patent Application No. PCT/KR2019/000784, filed on Jan. 18, 2019, which claims priority to Korean Patent Application No. 10-2018-0008259, filed Jan. 23, 2018, the disclosures of which are incorporated herein by reference in their entirety.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206132-0092-00US_Sequence_Listing_v2.txt" in ASCII format. The text file containing the Sequence Listing of the present application was created on Dec. 17, 2020 and is 842 bytes in size.

TECHNICAL FIELD

The present invention relates to a method for diagnosing cholangiocarcinoma through a bacterial metagenomic analysis and, more specifically, to a method of diagnosing cholangiocarcinoma, and the like by performing a bacterial metagenomic analysis using subject-derived samples to analyze an increase or decrease in the content of specific bacteria-derived extracellular vesicles.

BACKGROUND ART

Cholangiocarcinoma or bile duct cancer is a malignant tumor occurring in the intrahepatic or extrahepatic bile duct, and is used as a concept including gallbladder cancer. Histologically, most types of cholangiocarcinoma are adenocarcinoma. The cause of cholangiocarcinoma has not been clearly known so far. However, various biliary tract diseases are known to be associated with the development of cholangiocarcinoma, and it is expected that genetic and environmental factors are involved in the development of cholangiocarcinoma. Risk factors include primary sclerosing cholangitis, ulcerative colitis, choledochal cyst and clonorchis sinensis. Early diagnosis of cholangiocarcinoma is difficult because there are no symptoms. Sometimes cholangiocarcinoma is diagnosed after cholecystectomy for suspected cholelithiasis due to a non-specific symptom or abnormal liver function, and recently, due to the spread of medical examinations, cholangiocarcinoma is often diagnosed by chance through abdominal ultrasonography.

Meanwhile, it is known that the number of microorganisms symbiotically living in the human body is 100 trillion which is 10 times the number of human cells, and the number of genes of microorganisms exceeds 100 times the number of human genes. A microbiota is a microbial community that includes bacteria, archaea, and eukaryotes present in a given habitat. The intestinal microbiota is known to play a vital role in human's physiological phenomena and significantly affect human health and diseases through interactions with human cells. Bacteria coexisting in human bodies secrete nanometer-sized vesicles to exchange information about genes, proteins, low molecular weight compound, and the like with other cells. The mucous membranes form a physical barrier membrane that does not allow particles with the size of 200 nm or more to pass therethrough, and thus bacteria symbiotically living in the mucous membranes are unable to pass therethrough, but bacteria-derived extracellular vesicles have a size of approximately 100 nm or less and thus relatively freely pass through the mucous membranes and are absorbed into the human body.

Metagenomics, also called environmental genomics, may be analytics for metagenomic data obtained from samples collected from the environment. Recently, the bacterial composition of human microbiota has been listed using a method based on 16s ribosomal RNA (16s rRNA) base sequences, and 16s rDNA base sequences, which are genes of 16s ribosomal RNA, are analyzed using a next generation sequencing (NGS) platform (Nature. 2007 Oct. 18; 449 (7164): 804-810). However, as for the occurrence of cholangiocarcinoma, there is no report about a method of identifying, from a human-derived material such as blood, a causative factor of cholangiocarcinoma by analysis of metagenomes present in bacteria-derived vesicles and of diagnosing cholangiocarcinoma.

DISCLOSURE

Technical Problem

The present inventors extracted genes from bacteria-derived extracellular vesicles present in blood as subject-derived samples and performed a metagenomic analysis in this regard in order to diagnose the causal factors and risk of cholangiocarcinoma in advance, and as a result, identified bacteria-derived extracellular vesicles which may act as a causal factor of cholangiocarcinoma, thereby completing the present invention based on this.

Therefore, an object of the present invention is to provide a method of providing information for diagnosing cholangiocarcinoma through the metagenomic analysis of bacteria-derived extracellular vesicles.

However, the technical goals of the present invention are not limited to the aforementioned goals, and other unmentioned technical goals will be clearly understood by those of ordinary skill in the art from the following description.

Technical Solution

To achieve the above-described object of the present invention, there is provided a method of providing information for cholangiocarcinoma diagnosis, comprising the following processes:
(a) extracting DNAs from extracellular vesicles isolated from subject samples;
(b) performing polymerase chain reaction (PCR) on the extracted DNA using a pair of primers comprising SEQ ID NO: 1 and SEQ ID NO: 2; and
(c) comparing an increase or decrease in content of bacteria-derived extracellular vesicles of the subject-derived sample with that of a normal individual-derived sample through sequencing of a product of the PCR.

The present invention also provides a method of diagnosing cholangiocarcinoma, comprising the following processes:
(a) extracting DNAs from extracellular vesicles isolated from subject samples;

(b) performing polymerase chain reaction (PCR) on the extracted DNA using a pair of primers comprising SEQ ID NO: 1 and SEQ ID NO: 2; and (c) comparing an increase or decrease in content of bacteria-derived extracellular vesicles of the subject-derived sample with that of a normal individual-derived sample through sequencing of a product of the PCR.

The present invention also provides a method of predicting a risk for cholangiocarcinoma, comprising the following processes:

(a) extracting DNAs from extracellular vesicles isolated from subject samples;

(b) performing polymerase chain reaction (PCR) on the extracted DNA using a pair of primers comprising SEQ ID NO: 1 and SEQ ID NO: 2; and (c) comparing an increase or decrease in content of bacteria-derived extracellular vesicles of the subject-derived sample with that of a normal individual-derived sample through sequencing of a product of the PCR.

In one embodiment of the present invention, in process (c), the cholangiocarcinoma may be diagnosed by comparing an increase or decrease in content of extracellular vesicles derived from one or more bacteria selected from the group consisting of the phylum Deferribacteres and the phylum Verrucomicrobia.

In another embodiment of the present invention, in process (c), the cholangiocarcinoma may be diagnosed by comparing an increase or decrease in content of extracellular vesicles derived from one or more bacteria selected from the group consisting of the class Deferribacteres and the class Verrucomicrobiae.

In another embodiment of the present invention, in process (c), the cholangiocarcinoma may be diagnosed by comparing an increase or decrease in content of extracellular vesicles derived from one or more bacteria selected from the group consisting of the order Deferribacterales, the order Verrucomicrobiales, and the order RF32.

In another embodiment of the present invention, in process (c), the cholangiocarcinoma may be diagnosed by comparing an increase or decrease in content of extracellular vesicles derived from one or more bacteria selected from the group consisting of the family Bifidobacteriaceae, the family Halomonadaceae, the family Deferribacteraceae, the family Verrucomicrobiaceae, and the family Peptococcaceae.

In another embodiment of the present invention, in process (c), the cholangiocarcinoma may be diagnosed by comparing an increase or decrease in content of extracellular vesicles derived from one or more bacteria selected from the group consisting of the genus *Cupriavidus*, the genus *Parabacteroides*, the genus *Oscillospira*, the genus *Lactococcus*, the genus *Mucispirillum*, the genus *Akkermansia*, the genus *Dorea*, and the genus *Chromohalobacter*.

In another embodiment of the present invention, in comparison with the normal individual-derived sample, it is possible to diagnose an increase in the content of the following as cholangiocarcinoma:

extracellular vesicles derived from one or more bacteria selected from the group consisting of the phylum Deferribacteres and the phylum Verrucomicrobia, extracellular vesicles derived from one or more bacteria selected from the group consisting of the class Deferribacteres and the class Verrucomicrobiae, extracellular vesicles derived from one or more bacteria selected from the group consisting of the order Deferribacterales, the order Verrucomicrobiales, and the order RF32, extracellular vesicles derived from one or more bacteria selected from the group consisting of the family Halomonadaceae, the family Deferribacteraceae, the family Verrucomicrobiaceae, and the family Peptococcaceae, or extracellular vesicles derived from one or more bacteria selected from the group consisting of the genus *Parabacteroides*, the genus *Oscillospira*, the genus *Lactococcus*, the genus *Mucispirillum*, the genus *Akkermansia*, the genus *Dorea*, and the genus *Chromohalobacter*.

In another embodiment of the present invention, in process (c), in comparison with the normal individual-derived sample, it is possible to diagnose a decrease in the content of the following as cholangiocarcinoma:

extracellular vesicles derived from bacteria of the family Bifidobacteriaceae, or extracellular vesicles derived from bacteria of the genus *Cupriavidus*.

In another embodiment of the present invention, in process (c), in comparison with the normal individual-derived sample, cholangiocarcinoma may be diagnosed when contents of vesicles derived from bacteria of the genus *Akkermansia*, the genus *Dorea*, and the genus *Parabacteroides* are increased, and content of vesicles derived from bacteria of the genus *Cupriavidus* is decreased.

In another embodiment of the present invention, in process (c), in comparison with the normal individual-derived sample, cholangiocarcinoma may be diagnosed when contents of vesicles derived from bacteria of the genus *Akkermansia*, the genus *Dorea*, and the genus *Parabacteroides* are increased, and content of vesicles derived from bacteria of the genus *Cupriavidus* is decreased; and contents of extracellular vesicles derived from one or more bacteria selected from the group consisting of the phylum Deferribacteres and the phylum Verrucomicrobia, extracellular vesicles derived from one or more bacteria selected from the group consisting of the class Deferribacteres and the class Verrucomicrobiae, extracellular vesicles derived from one or more bacteria selected from the group consisting of the order Deferribacterales and the order Verrucomicrobiales, extracellular vesicles derived from one or more bacteria selected from the group consisting of the family Halomonadaceae, the family Deferribacteraceae, the family Verrucomicrobiaceae, and the family Peptococcaceae, or extracellular vesicles derived from one or more bacteria selected from the group consisting of the genus *Oscillospira*, the genus *Lactococcus*, the genus *Mucispirillum*, and the genus *Chromohalobacter* are increased.

In another embodiment of the present invention, in process (c), in comparison with the normal individual-derived sample, cholangiocarcinoma may be diagnosed when contents of vesicles derived from bacteria of the genus *Akkermansia*, the genus *Dorea*, and the genus *Parabacteroides* are increased, and content of vesicles derived from bacteria of the genus *Cupriavidus* is decreased; and content of extracellular vesicles derived from bacteria of the family Bifidobacteriaceae is decreased.

In another embodiment of the present invention, the subject sample may be blood.

In another embodiment of the present invention, the blood may be whole blood, serum, plasma, or blood mononuclear cells.

Advantageous Effects

Extracellular vesicles secreted from bacteria present in the environment are absorbed into the body, and can directly affect the occurrence of cancer, and cholangiocarcinoma is difficult to diagnose early before symptoms appear so that effective treatment is difficult. Therefore, by previous diagnosis of causative factors and the risk for the onset of cholangiocarcinoma through metagenomic analysis of bacteria-derived extracellular vesicles using human-derived samples according to the present invention, the risk group of cholangiocarcinoma can be diagnosed and predicted early to delay or prevent the onset of cholangiocarcinoma through proper management, and early diagnosis can be performed even after the onset, thereby reducing the incidence of cholangiocarcinoma and increasing the therapeutic effect. In addition, the progression of cancer can be improved or the recurrence of cancer may be prevented by avoiding the exposure of causative factors through metagenomic analysis for patients diagnosed with cholangiocarcinoma.

DESCRIPTION OF DRAWINGS

FIG. 1A illustrates images showing the distribution pattern of bacteria and extracellular vesicles over time after intestinal bacteria and bacteria-derived extracellular vesicles (EVs) were orally administered to mice.

BEST MODE

Figure 1B:
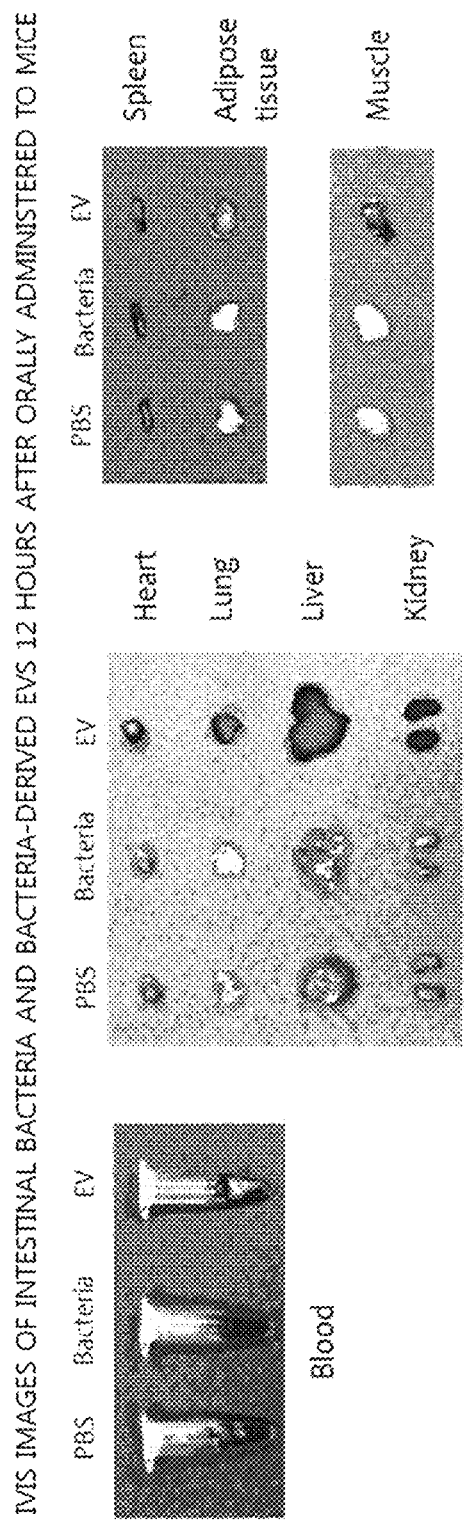
FIG. 1B illustrates images showing the distribution pattern of bacteria and EVs after being orally administered to mice and, at 12 hours, blood and various organs were extracted.

The present invention relates to a method of diagnosing cholangiocarcinoma through bacterial metagenomic analysis. The inventors of the present invention extracted genes from bacteria-derived extracellular vesicles using a subject-derived sample, performed metagenomic analysis thereon, and identified bacteria-derived extracellular vesicles capable of acting as a causative factor of cholangiocarcinoma.

Therefore, the present invention provides a method of providing information for diagnosing cholangiocarcinoma, the method comprising:
(a) extracting DNAs from extracellular vesicles isolated from subject samples;
(b) performing polymerase chain reaction (PCR) on the extracted DNA using a pair of primers comprising SEQ ID NO: 1 and SEQ ID NO: 2; and
(c) comparing an increase or decrease in content of bacteria-derived extracellular vesicles of the subject-derived sample with that of a normal individual-derived sample through sequencing of a product of the PCR.

The term "cholangiocarcinoma diagnosis" as used herein refers to determining whether a patient has a risk for cholangiocarcinoma, whether the risk for cholangiocarcinoma is relatively high, or whether cholangiocarcinoma has already occurred. The method of the present invention may be used to delay the onset of cholangiocarcinoma through special and appropriate care for a specific patient, which is a patient having a high risk for cholangiocarcinoma or prevent the onset of cholangiocarcinoma. In addition, the method may be clinically used to determine treatment by selecting the most appropriate treatment method through early diagnosis of cholangiocarcinoma.

Meanwhile, the term "cholangiocarcinoma" used herein is a malignant tumor occurring in the intrahepatic or extrahepatic bile duct, and may be interchangeably used with "bile duct cancer."

The term "metagenome" as used herein refers to the total of genomes including all viruses, bacteria, fungi, and the like in isolated regions such as soil, the intestines of animals, and the like, and is mainly used as a concept of genomes that explains identification of many microorganisms at once using a sequencer to analyze non-cultured microorganisms. In particular, a metagenome does not refer to a genome of one species, but refers to a mixture of genomes, including genomes of all species of an environmental unit. This term originates from the view that, when defining one species in a process in which biology is advanced into omics, various species as well as existing one species functionally interact with each other to form a complete species. Technically, it is the subject of techniques that analyzes all DNAs and RNAs regardless of species using rapid sequencing to identify all species in one environment and verify interactions and metabolism. In the present invention, bacterial metagenomic analysis is performed using bacteria-derived extracellular vesicles isolated from, for example, serum.

In the present invention, the subject sample may be blood, and the blood may be whole blood, serum, plasma, or blood mononuclear cells, but the present invention is not limited thereto.

In an embodiment of the present invention, metagenomic analysis is performed on the bacteria-derived extracellular vesicles, and bacteria-derived vesicles capable of acting as a cause of the onset of cholangiocarcinoma were actually identified by analysis at phylum, class, order, family, and genus levels.

More particularly, in one embodiment of the present invention, as a result of performing bacterial metagenomic analysis on vesicles present in subject-derived blood samples at a phylum level, the content of extracellular vesicles derived from bacteria belonging to the phylum Deferribacteres and the phylum Verrucomicrobia was significantly different between cholangiocarcinoma patients and normal individuals (see Example 4).

More particularly, in one embodiment of the present invention, as a result of performing bacterial metagenomic analysis on vesicles present in subject-derived blood samples at a class level, the content of extracellular vesicles derived from bacteria belonging to the class Deferribacteres and the class Verrucomicrobiae was significantly different between cholangiocarcinoma patients and normal individuals (see Example 4).

More particularly, in one embodiment of the present invention, as a result of performing bacterial metagenomic analysis on vesicles present in subject-derived blood samples at an order level, the content of extracellular vesicles derived from bacteria belonging to the order Deferribacterales, the order Verrucomicrobiales, and the order RF32 was significantly different between cholangiocarcinoma patients and normal individuals (see Example 4).

More particularly, in one embodiment of the present invention, as a result of performing bacterial metagenomic analysis on vesicles present in subject-derived blood samples at a family level, the content of extracellular vesicles derived from bacteria belonging to the family Bifidobacteriaceae, the family Halomonadaceae, the family Deferribacteraceae, the family Verrucomicrobiaceae, and the family Peptococcaceae was significantly different between cholangiocarcinoma patients and normal individuals (see Example 4).

More particularly, in one embodiment of the present invention, as a result of performing bacterial metagenomic analysis on vesicles present in subject-derived blood samples at a genus level, the content of extracellular vesicles derived from bacteria belonging to the genus *Cupriavidus*, the genus *Parabacteroides*, the genus *Oscillospira*, the genus *Lactococcus*, the genus *Mucispirillum*, the genus *Akkermansia*, the genus *Dorea*, and the genus *Chromohalobacter* was significantly different between cholangiocarcinoma patients and normal individuals (see Example 4).

Through the results of the examples, it was confirmed that distribution variables of the identified bacteria-derived extracellular vesicles could be usefully used for the prediction of the onset of cholangiocarcinoma.

MODES OF THE INVENTION

Hereinafter, the present invention will be described with reference to exemplary examples to aid in understanding of the present invention. However, these examples are provided only for illustrative purposes and are not intended to limit the scope of the present invention.

EXAMPLES

Example 1

Analysis of In Vivo Absorption, Distribution, and Excretion Patterns of Intestinal Bacteria and Bacteria-Derived Vesicles To evaluate whether intestinal bacteria and bacteria-derived vesicles are absorbed systemically through the mucosa, an experiment was performed using the following method. 50 µg of each of intestinal bacteria and the intestinal bacteria-derived extracellular vesicles (EVs), labeled with fluorescence, were administered to the gastrointestinal tracts of mice, and fluorescence was measured at 0 h, and after 5 min, 3 h, 6 h, and 12 h. As a result of observing the entire images of mice, as illustrated in FIG. 1A, the bacteria were not systematically absorbed when administered, while the bacteria-derived EVs were systematically absorbed at 5 min after administration, and, at 3 h after administration, fluorescence was strongly observed in the bladder, from which it was confirmed that the EVs were excreted via the urinary system, and were present in the bodies up to 12 h after administration.

After intestinal bacteria and intestinal bacteria-derived extracellular vesicles were systematically absorbed, to evaluate a pattern of invasion of intestinal bacteria and the bacteria-derived EVs into various organs in the human body after being systematically absorbed, 50 µg of each of the bacteria and bacteria-derived EVs, labeled with fluorescence, were administered using the same method as that used above, and then, at 12 h after administration, blood, the heart, the lungs, the liver, the kidneys, the spleen, adipose tissue, and muscle were extracted from each mouse. As a result of observing fluorescence in the extracted tissues, as illustrated in FIG. 1B, it was confirmed that the intestinal bacteria were not absorbed into each organ, while the intestinal bacteria-derived EVs were distributed in the blood, heart, lungs, liver, kidneys, spleen, adipose tissue, and muscle.

Example 2

Vesicle Isolation and DNA Extraction from Blood

To isolate vesicles and extract DNA, from blood, first, blood was added to a 10 ml tube and centrifuged at 3,500×g and 4□ for 10 min to precipitate a suspension, and only a supernatant was collected, which was then placed in a new 10 ml tube. The collected supernatant was filtered using a 0.22 µm filter to remove bacteria and impurities, and then placed in centrifugal filters (50 kD) and centrifuged at 1500×g and 4□ for 15 min to discard materials with a smaller size than 50 kD, and then concentrated to 10 ml. Once again, bacteria and impurities were removed therefrom using a 0.22 µm filter, and then the resulting concentrate was subjected to ultra-high speed centrifugation at 150,000×g and 4□ for 3 hours by using a Type 90ti rotor to remove a supernatant, and the agglomerated pellet was dissolved with phosphate-buffered saline (PBS), thereby obtaining vesicles.

100 µl of the extracellular vesicles isolated from the blood according to the above-described method was boiled at 100□ to allow the internal DNA to come out of the lipid and then cooled on ice for 5 minutes. Next, the resulting vesicles were centrifuged at 10,000×g and 4□ for 30 minutes to remove the remaining suspension, only the supernatant was collected, and then the amount of DNA extracted was quantified using a NanoDrop sprectrophotometer. In addition, to verify whether bacteria-derived DNA was present in the extracted DNA, PCR was performed using 16s rDNA primers shown in Table 1 below.

TABLE 1

| Primer | | Sequence | SEQ ID NO. |
|---|---|---|---|
| 16S rDNA | 16S_V3_F | 5-TCGTCGGCAGCGTC AGATGTGTATAAGAG ACAGCCTACGGGNGG CWGCAG-3' | 1 |

TABLE 1-continued

| Primer | Sequence | SEQ ID NO. |
|---|---|---|
| 16S_V4_R | 5-GTCTCGTGGGCTCG GAGATGTGTATAAGA GACAGGACTACHVGG GTATCTAATCC-3' | 2 |

Example 3

Metagenomic Analysis Using DNA Extracted from Blood

DNA was extracted using the same method as that used in Example 2, and then PCR was performed thereon using 16S rDNA primers shown in Table 1 to amplify DNA, followed by sequencing (Illumina MiSeq sequencer). The results were output as standard flowgram format (SFF) files, and the SFF files were converted into sequence files (.fasta) and nucleotide quality score files using GS FLX software (v2.9), and then credit rating for reads was identified, and portions with a window (20 bps) average base call accuracy of less than 99% (Phred score <20) were removed. After removing the low-quality portions, only reads having a length of 300 bps or more were used (Sickle version 1.33), and for operational taxonomy unit (OTU) analysis, clustering was performed using UCLUST and USEARCH according to sequence similarity. In particular, clustering was performed based on sequence similarity values of 94% for genus, 90% for family, 85% for order, 80% for class, and 75% for phylum, and phylum, class, order, family, and genus levels of each OTU were classified, and bacteria with a sequence similarity of 97% or more were analyzed (QIIME) using 16S DNA sequence databases (108,453 sequences) of BLASTN and GreenGenes.

Example 4

Cholangiocarcinoma Diagnostic Model Based on Metagenomic Analysis of Bacteria-Derived EVs Isolated from Blood EVs were isolated from blood samples of 79 cholangiocarcinoma patients and 259 normal individuals, the two groups matched in age and gender, and then metagenomic sequencing was performed thereon using the method of Example 3. For the development of a diagnostic model, first, a strain exhibiting a p value of less than 0.05 between two groups in a t-test and a difference of two-fold or more between two groups was selected, and then an area under curve (AUC), sensitivity, and specificity, which are diagnostic performance indexes, were calculated by logistic regression analysis.

Figure 2:
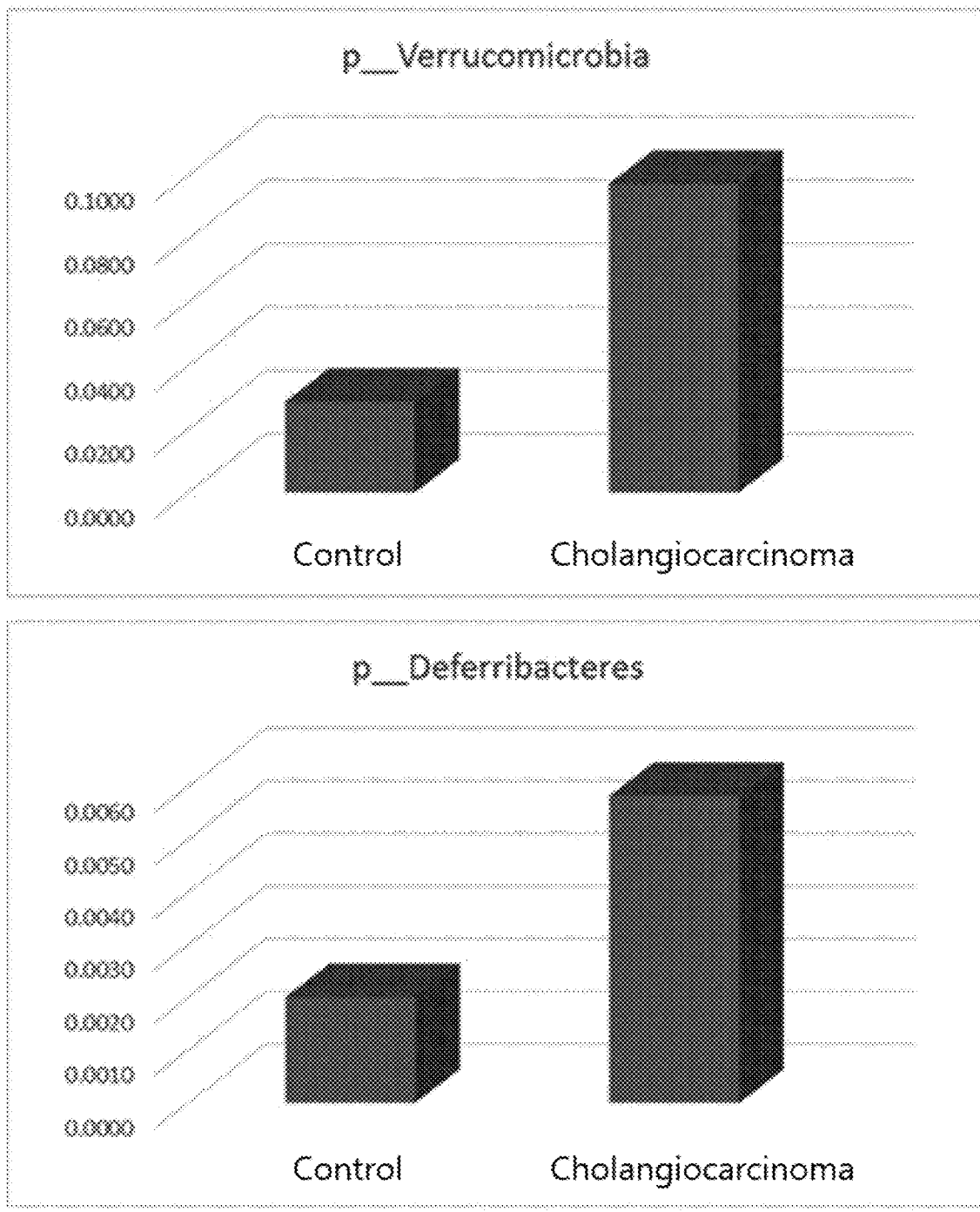
FIG. 2 is a result showing the distribution of bacteria-derived extracellular vesicles (EVs), which is significant in diagnostic performance at the phylum level by isolating bacteria-derived vesicles from blood of a patient with cholangiocarcinoma and a normal individual, and then performing a metagenomic analysis.

As a result of analyzing bacteria-derived EVs in blood at a phylum level, a diagnostic model developed using bacteria belonging to the phylum Deferribacteres and the phylum Verrucomicrobia as a biomarker exhibited significant diagnostic performance for cholangiocarcinoma (see Table 2 and FIG. 2).

TABLE 2

| Taxon | Control | | Cholangio-carcinoma | | t-test p-value | Ratio | Training Set | | | Test Set | | |
|---|---|---|---|---|---|---|---|---|---|---|---|---|
| | Mean | SD | Mean | SD | | | AUC | sensi-tivity | speci-ficity | AUC | sensi-tivity | speci-ficity |
| p_Deferribacteres | 0.0020 | 0.0069 | 0.0058 | 0.0109 | 0.0042 | 2.91 | 0.63 | 0.98 | 0.07 | 0.72 | 0.99 | 0.09 |
| p_Verrucomicrobia | 0.0286 | 0.0440 | 0.0973 | 0.0642 | 0.0000 | 3.40 | 0.81 | 0.96 | 0.39 | 0.91 | 0.99 | 0.55 |

Figure 3:
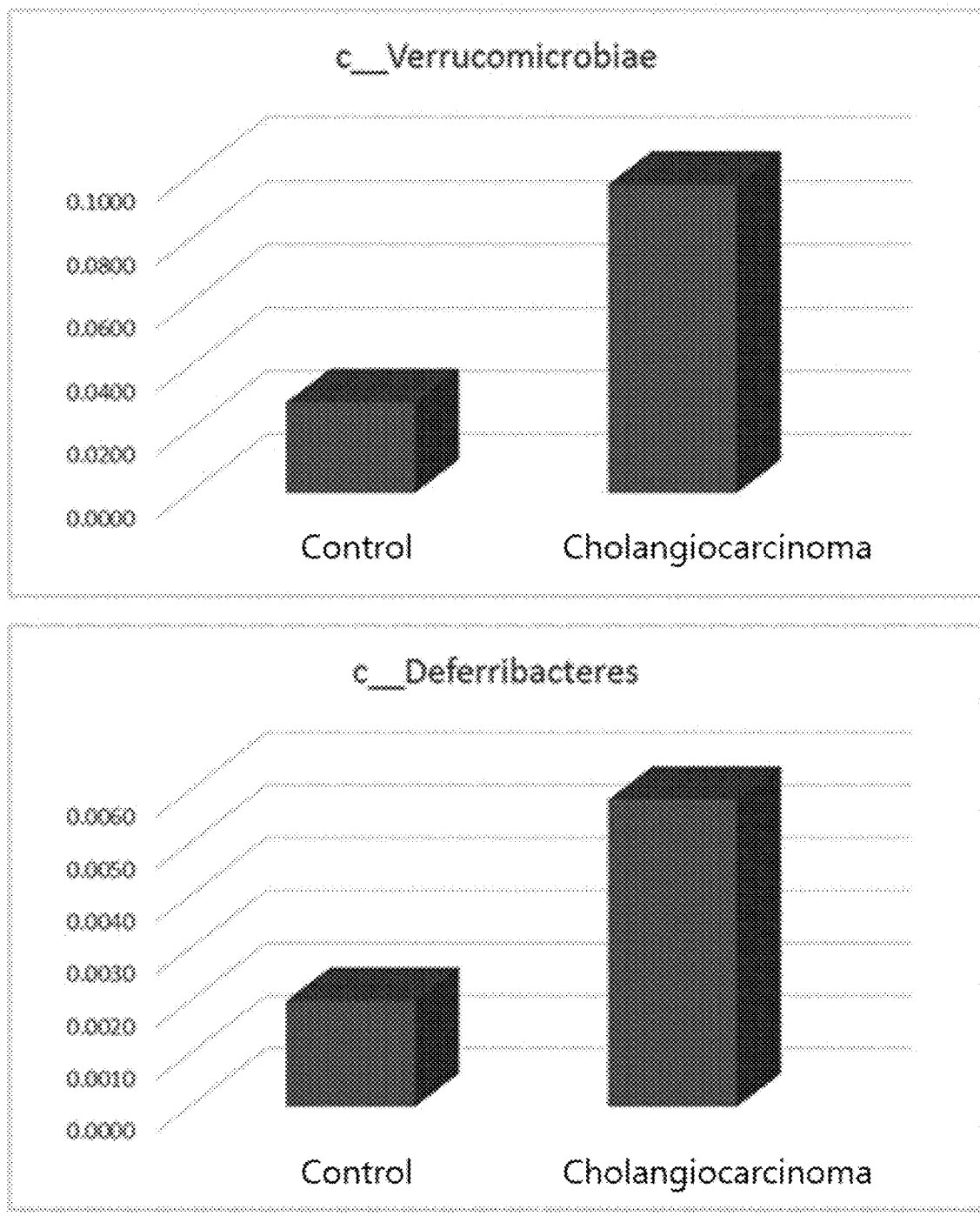
FIG. 3 is a result showing the distribution of bacteria-derived extracellular vesicles (EVs), which is significant in diagnostic performance at the class level by isolating bacteria-derived vesicles from blood of a patient with cholangiocarcinoma and a normal individual, and then performing a metagenomic analysis.

As a result of analyzing bacteria-derived EVs in blood at a class level, a diagnostic model developed using bacteria belonging to the class Deferribacteres and the class Verrucomicrobiae as a biomarker exhibited significant diagnostic performance for cholangiocarcinoma (see Table 3 and FIG. 3).

TABLE 3

| Taxon | Control | | Cholangio-carcinoma | | t-test p-value | Ratio | Training Set | | | Test Set | | |
|---|---|---|---|---|---|---|---|---|---|---|---|---|
| | Mean | SD | Mean | SD | | | AUC | sensi-tivity | speci-ficity | AUC | sensi-tivity | speci-ficity |
| c_Deferribacteres | 0.0020 | 0.0069 | 0.0058 | 0.0109 | 0.0042 | 2.91 | 0.63 | 0.98 | 0.07 | 0.72 | 0.99 | 0.09 |
| c_Verrucomicrobiae | 0.0285 | 0.0440 | 0.0973 | 0.0641 | 0.0000 | 3.42 | 0.81 | 0.96 | 0.39 | 0.91 | 0.99 | 0.55 |

Figure 4:
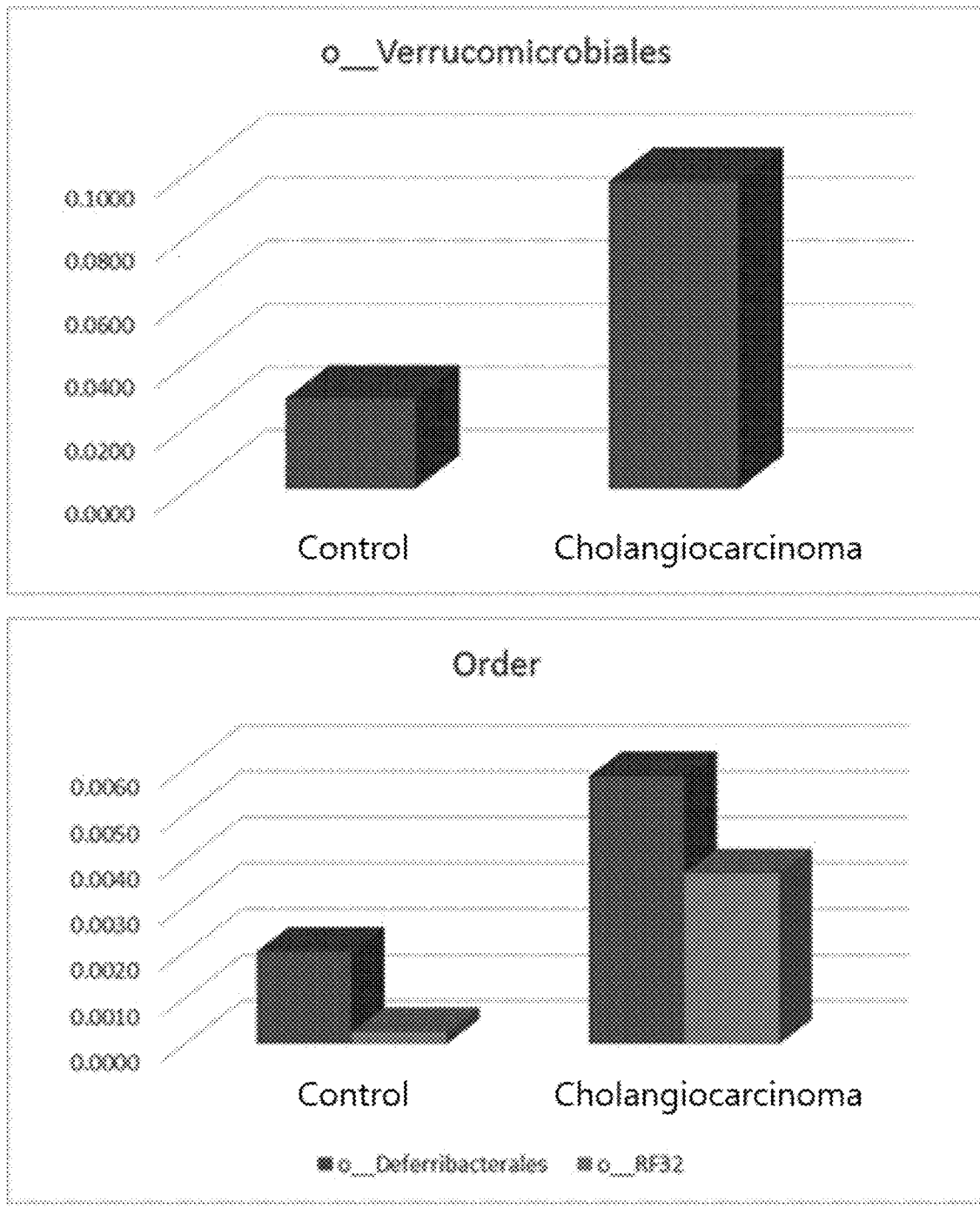
FIG. 4 is a result showing the distribution of bacteria-derived extracellular vesicles (EVs), which is significant in diagnostic performance at the order level by isolating bacteria-derived vesicles from blood of a patient with cholangiocarcinoma and a normal individual, and then performing a metagenomic analysis.

As a result of analyzing bacteria-derived EVs in blood at an order level, a diagnostic model developed using bacteria belonging to the order Deferribacterales, the order Verrucomicrobiales, and the order RF32 as a biomarker exhibited significant diagnostic performance for cholangiocarcinoma (see Table 4 and FIG. 4).

TABLE 4

| Taxon | Control | | Cholangio-carcinoma | | t-test p-value | Ratio | Training Set | | | Test Set | | |
|---|---|---|---|---|---|---|---|---|---|---|---|---|
| | Mean | SD | Mean | SD | | | AUC | sensi-tivity | speci-ficity | AUC | sensi-tivity | speci-ficity |
| o__Deferribacterales | 0.0020 | 0.0069 | 0.0058 | 0.0109 | 0.0042 | 2.91 | 0.59 | 0.99 | 0.04 | 0.74 | 0.99 | 0.08 |
| o__Verrucomicrobiales | 0.0285 | 0.0440 | 0.0973 | 0.0641 | 0.0000 | 3.42 | 0.86 | 0.96 | 0.43 | 0.78 | 0.95 | 0.48 |
| o__RF32 | 0.0002 | 0.0010 | 0.0037 | 0.0057 | 0.0000 | 14.94 | 0.72 | 0.98 | 0.33 | 0.76 | 0.99 | 0.36 |

Figure 5:
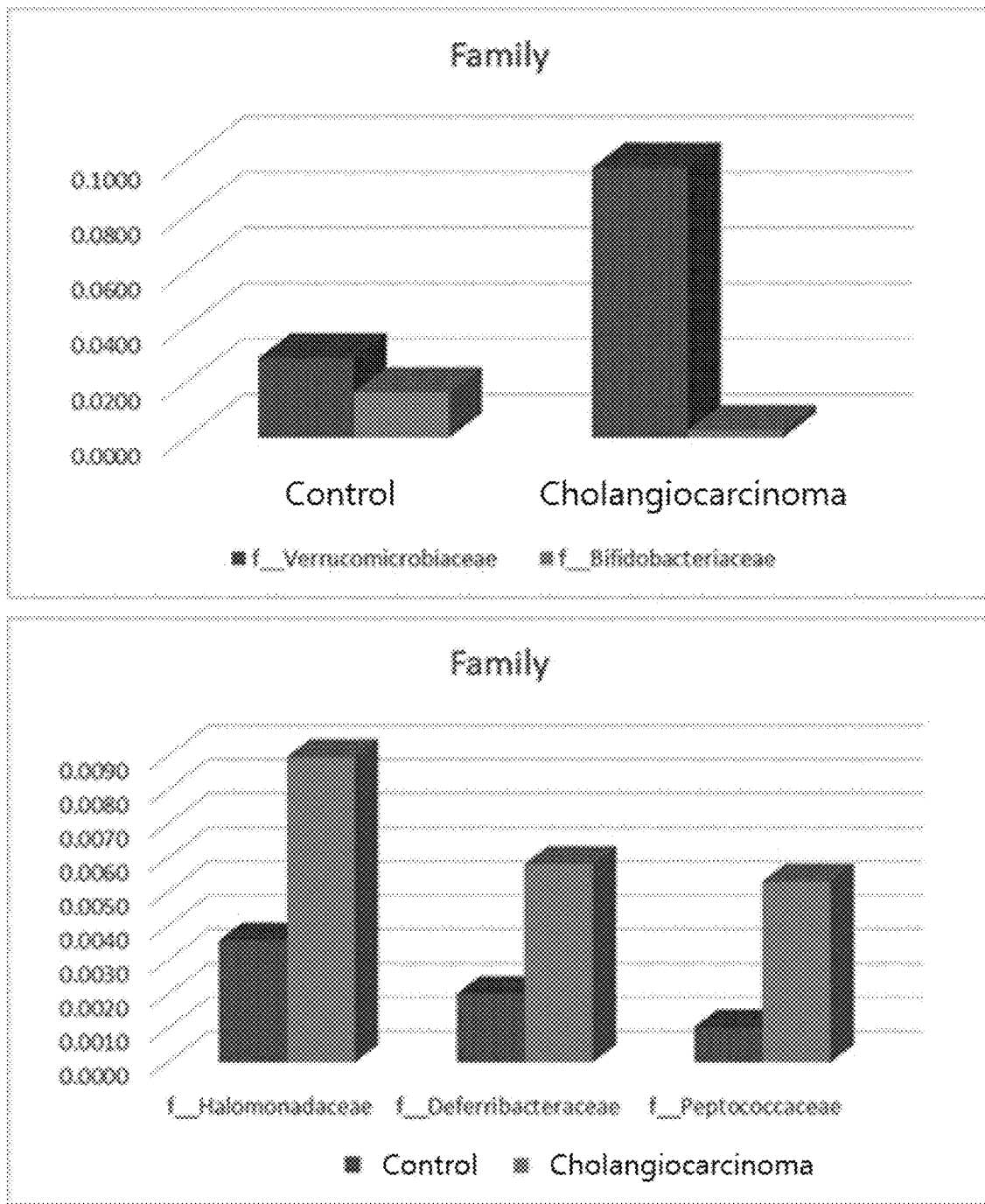
FIG. 5 is a result showing the distribution of bacteria-derived extracellular vesicles (EVs), which is significant in diagnostic performance at the family level by isolating bacteria-derived vesicles from blood of a patient with cholangiocarcinoma and a normal individual, and then performing a metagenomic analysis.

As a result of analyzing bacteria-derived EVs in blood at a family level, a diagnostic model developed using bacteria belonging to the family Bifidobacteriaceae, the family Halomonadaceae, the family Deferribacteraceae, the family Verrucomicrobiaceae, and the family Peptococcaceae as a biomarker exhibited significant diagnostic performance for cholangiocarcinoma (see Table 5 and FIG. 5).

TABLE 5

| Taxon | Control | | Cholangio-carcinoma | | t-test p-value | Ratio | Training Set | | | Test Set | | |
|---|---|---|---|---|---|---|---|---|---|---|---|---|
| | Mean | SD | Mean | SD | | | AUC | sensi-tivity | speci-ficity | AUC | sensi-tivity | speci-ficity |
| f__Bifidobacteriaceae | 0.0162 | 0.0209 | 0.0026 | 0.0051 | 0.0000 | 0.16 | 0.81 | 0.96 | 0.18 | 0.78 | 0.98 | 0.09 |
| f__Halomonadaceae | 0.0036 | 0.0073 | 0.0090 | 0.0132 | 0.0008 | 2.51 | 0.65 | 0.97 | 0.09 | 0.66 | 0.98 | 0.05 |
| f__Deferribacteraceae | 0.0020 | 0.0069 | 0.0058 | 0.0109 | 0.0042 | 2.91 | 0.63 | 0.98 | 0.07 | 0.72 | 0.99 | 0.09 |
| f__Verrucomicrobiaceae | 0.0285 | 0.0440 | 0.0973 | 0.0641 | 0.0000 | 3.42 | 0.81 | 0.96 | 0.39 | 0.91 | 0.99 | 0.55 |
| f__Peptococcaceae | 0.0010 | 0.0027 | 0.0053 | 0.0062 | 0.0000 | 5.17 | 0.70 | 0.97 | 0.26 | 0.83 | 0.96 | 0.50 |

Figure 6:
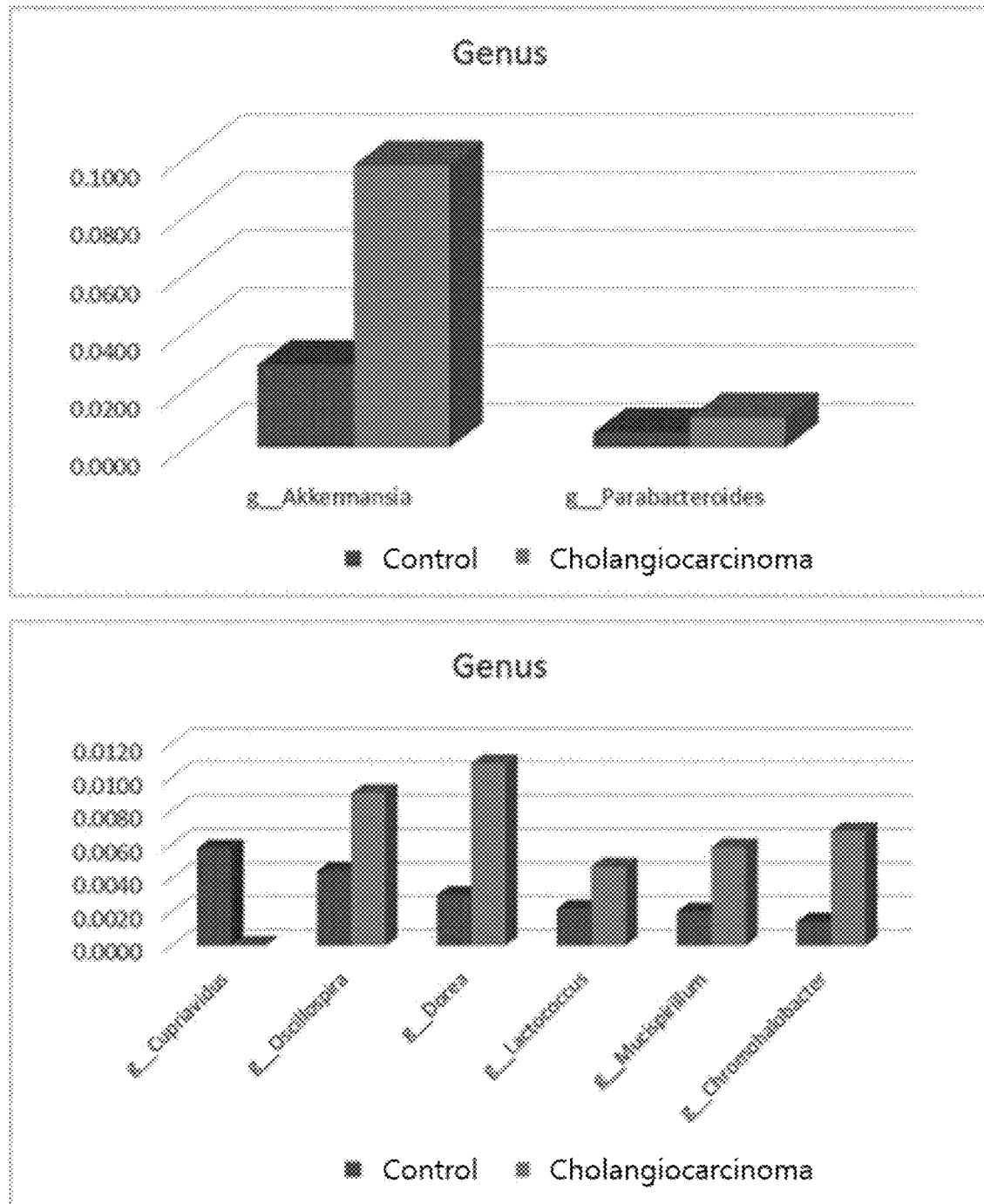
FIG. 6 is a result showing the distribution of bacteria-derived extracellular vesicles (EVs), which is significant in diagnostic performance at the genus level by isolating bacteria-derived vesicles from blood of a patient with cholangiocarcinoma and a normal individual, and then performing a metagenomic analysis.

As a result of analyzing bacteria-derived EVs in blood at a genus level, a diagnostic model developed using bacteria belonging to the genus *Cupriavidus*, the genus *Parabacteroides*, the genus *Oscillospira*, the genus *Lactococcus*, the genus *Mucispirillum*, the genus *Akkermansia*, the genus *Dorea*, and the genus *Chromohalobacter* as a biomarker exhibited significant diagnostic performance for cholangiocarcinoma (see Table 6 and FIG. 6).

TABLE 6

| Taxon | Control | | Cholangio-carcinoma | | t-test p-value | Ratio | Training Set | | | Test Set | | |
|---|---|---|---|---|---|---|---|---|---|---|---|---|
| | Mean | SD | Mean | SD | | | AUC | sensi-tivity | speci-ficity | AUC | sensi-tivity | speci-ficity |
| g__Cupriavidus | 0.0058 | 0.0135 | 0.0000 | 0.0002 | 0.0000 | 0.01 | 0.76 | 1.00 | 0.04 | 0.79 | 0.99 | 0.00 |
| g__Parabacteroides | 0.0051 | 0.0068 | 0.0103 | 0.0110 | 0.0002 | 2.01 | 0.63 | 0.98 | 0.09 | 0.70 | 0.96 | 0.18 |
| g__Oscillospira | 0.0044 | 0.0068 | 0.0090 | 0.0098 | 0.0002 | 2.04 | 0.62 | 0.98 | 0.07 | 0.71 | 0.95 | 0.14 |
| g__Lactococcus | 0.0022 | 0.0047 | 0.0047 | 0.0056 | 0.0001 | 2.14 | 0.60 | 0.98 | 0.04 | 0.69 | 0.96 | 0.09 |
| g__Mucispirillum | 0.0020 | 0.0069 | 0.0058 | 0.0109 | 0.0042 | 2.91 | 0.63 | 0.98 | 0.07 | 0.72 | 0.99 | 0.09 |
| g__Akkermansia | 0.0284 | 0.0440 | 0.0973 | 0.0642 | 0.0000 | 3.42 | 0.81 | 0.96 | 0.39 | 0.91 | 0.99 | 0.55 |
| g__Dorea | 0.0030 | 0.0051 | 0.0108 | 0.0145 | 0.0000 | 3.61 | 0.68 | 0.98 | 0.23 | 0.77 | 0.96 | 0.36 |
| g__Chromohalobacter | 0.0014 | 0.0048 | 0.0068 | 0.0122 | 0.0003 | 4.79 | 0.68 | 0.98 | 0.18 | 0.74 | 0.99 | 0.05 |

The above description of the present invention is provided only for illustrative purposes, and it will be understood by one of ordinary skill in the art to which the present invention pertains that the invention may be embodied in various modified forms without departing from the spirit or essential characteristics thereof. Thus, the embodiments described herein should be considered in an illustrative sense only and not for the purpose of limitation.

INDUSTRIAL APPLICABILITY

The method of providing information for diagnosing cholangiocarcinoma through a bacterial metagenomic analysis according to the present invention may be used for predicting the risk of cholangiocarcinoma onset and diagnosing cholangiocarcinoma by performing a bacterial metagenomic analysis using subject-derived samples to analyze an increase or decrease in the content of specific bacteria-derived extracellular vesicles.

The invention claimed is:

1. A method of providing information for diagnosing cholangiocarcinoma, the method comprising:
   (a) isolating bacteria-derived extracellular vesicles from blood samples obtained from a subject who is suspected of being at risk of developing cholangiocarcinoma and from a normal individual, and extracting DNAs from bacteria-derived extracellular vesicles isolated from the samples;
   (b) detecting the content of extracellular vesicles in the samples by performing polymerase chain reaction (PCR) on the extracted DNA using a pair of primers comprising SEQ ID NO: 1 and SEQ ID NO: 2;
   (c) performing metagenomic sequencing on the product of the PCR to determine content of bacteria-derived extracellular vesicles in each sample;
   (d) selecting bacteria-derived extracellular vesicles exhibiting a p-value less than 0.05 between the two groups in a t-test and a mean value difference of two-fold or more between two groups, and
   (e) forming a diagnostic model for cholangiocarcinoma consisting of the extracellular vesicles derived from: (i) the genus *Cupriavidus*, and (ii) the genus *Parabacteroides*, the genus *Oscillospira*, the genus *Lactococcus*, the genus *Mucispirillum*, the genus *Akkermansia*, the genus *Dorea*, and the genus *Chromohalobacter*,
   wherein in the diagnostic model, an increase in the content of the extracellular vesicles derived from the genus *Parabacteroides*, the genus *Oscillospira*, the genus *Lactococcus*, the genus *Mucispirillum*, the genus *Akkermansia*, the genus *Dorea*, and the genus *Chromohalobacter* by two-fold or more and a decrease in the content of the extracellular vesicles derived from the genus *Cupriavidus* by two-fold or more in the sample from the subject, in comparison with the content of extracellular vesicles in the sample from the normal individual, indicate a risk of developing cholangiocarcinoma.

2. The method of claim 1, wherein the blood is whole blood, serum, plasma, or blood mononuclear cells.

3. A method of providing information for diagnosing cholangiocarcinoma, the method comprising:
   (a) isolating bacteria-derived extracellular vesicles from a blood sample obtained from a subject who is suspected of being at risk of developing cholangiocarcinoma and from a normal individual group;
   (b) extracting DNAs from the bacteria-derived extracellular vesicles isolated from the samples;
   (c) detecting the content of extracellular vesicles in the samples by performing polymerase chain reaction (PCR) on the extracted DNA using a pair of primers comprising SEQ ID NO: 1 and SEQ ID NO: 2, and then performing metagenomic sequencing of the product of the PCR to determine content of bacteria-derived extracellular vesicles in each sample;

(d) selecting strains exhibiting a p-value less than 0.05 between the two groups in a t-test and a mean value difference of two-fold or more between two groups; and
(e) forming a diagnostic model for cholangiocarcinoma consisting of the extracellular vesicles derived the genus *Cupriavidus*, the genus *Akkermansia*, and the genus *Dorea*, wherein Area Under the Curve (AUC) value of the three extracellular vesicles is 0.77 or higher, calculated by logistic regression analysis, and wherein the increase in the content of the extracellular vesicles derived from the genus *Parabacteroides*, the genus *Oscillospira*, the genus *Lactococcus*, the genus *Mucispirillum*, the genus *Akkermansia*, the genus *Dorea*, and the genus *Chromohalobacter* by two-fold or more and the decrease in the content of the extracellular vesicles derived from the genus *Cupriavidus* by two-fold or more in the sample from the subject, in comparison with the content of extracellular vesicles in the sample from the normal individual, indicate a risk of developing cholangiocarcinoma.

\* \* \* \* \*